(12) United States Patent
Aharon

(10) Patent No.: US 9,377,395 B2
(45) Date of Patent: Jun. 28, 2016

(54) OPTICAL POLARIMETRIC IMAGING

(76) Inventor: Ofir Aharon, Ofakim (IL)

( * ) Notice: Subject to any disclaimer, the term of this patent is extended or adjusted under 35 U.S.C. 154(b) by 405 days.

(21) Appl. No.: 13/982,263

(22) PCT Filed: Jan. 31, 2012

(86) PCT No.: PCT/IB2012/050444
§ 371 (c)(1),
(2), (4) Date: Jul. 28, 2013

(87) PCT Pub. No.: WO2012/104784
PCT Pub. Date: Aug. 9, 2012

(65) Prior Publication Data
US 2013/0307950 A1 Nov. 21, 2013

Related U.S. Application Data

(60) Provisional application No. 61/437,693, filed on Jan. 31, 2011.

(51) Int. Cl.
*G01J 4/00* (2006.01)
*G01N 21/21* (2006.01)
(Continued)

(52) U.S. Cl.
CPC .............. *G01N 21/21* (2013.01); *A61B 5/0077* (2013.01); *A61B 5/444* (2013.01); *G01N 21/4738* (2013.01); *A61B 5/0064* (2013.01); *A61B 5/7239* (2013.01)

(58) Field of Classification Search
CPC ............ G01N 21/21; G01N 2021/216; G01N 21/4738; G01N 21/4795; G01N 21/47
USPC .......................................... 356/369; 600/425
See application file for complete search history.

(56) References Cited

U.S. PATENT DOCUMENTS 3,882,454 A * 5/1975 Marie ...................... G06K 9/74
250/214 VT
5,432,607 A * 7/1995 Taubenblatt ......... G01N 21/956
250/206.1
5,847,394 A * 12/1998 Alfano .................... A61B 1/042
250/341.1

(Continued)

FOREIGN PATENT DOCUMENTS

WO       2009097618 A1      8/2009

OTHER PUBLICATIONS

Informal Comments in response to Written Opinion of the International Searching Authority of PCT/IB2012/050444.
(Continued)

*Primary Examiner* — Sath V Perungavoor
*Assistant Examiner* — Nathnael Aynalem
(74) *Attorney, Agent, or Firm* — Dr. Hanan Farber Patent Agent Ltd.

(57) ABSTRACT

A method for probing morphology of a tissue surface using a system which may include a light source, a polarizer, an analyzer, and a camera with a plurality of picture elements. The method illuminates the tissue surface with incident light through the polarizer. The camera may capture through the analyzer, scattered light from the tissue surface in a continuous sequence of image frames. Variation of polarization state may be of at least one of (1) the incident light from the light source by varying the polarizer or (2) the scattered light from the tissue surface by varying the analyzer. During the capture, for a picture element of the camera, a varying intensity signal of the scattered light is detected responsive to the varying polarization state.

19 Claims, 11 Drawing Sheets

(51) Int. Cl.
*G01N 21/47* (2006.01)
*A61B 5/00* (2006.01)

(56) References Cited

U.S. PATENT DOCUMENTS

| | | | |
|---|---|---|---|
| 6,516,084 B2 | 2/2003 | Shepard | |
| 6,587,711 B1 | 7/2003 | Alfano | |
| 7,289,211 B1 | 10/2007 | Walsh, Jr. et al. | |
| 7,460,248 B2 | 12/2008 | Kurtz et al. | |
| 2002/0044679 A1 | 4/2002 | Shepard | |
| 2005/0240107 A1* | 10/2005 | Alfano | A61B 5/0059 600/476 |
| 2006/0066843 A1 | 3/2006 | Guetta et al. | |
| 2006/0147095 A1* | 7/2006 | Usher | G06K 9/00604 382/117 |
| 2006/0164643 A1* | 7/2006 | Giakos | G01J 3/02 356/369 |
| 2007/0211928 A1 | 9/2007 | Weng et al. | |
| 2007/0263226 A1 | 11/2007 | Kurtz et al. | |
| 2007/0296958 A1* | 12/2007 | Zou | G01N 21/21 356/73 |
| 2008/0137094 A1* | 6/2008 | Teramura | G01B 9/02004 356/489 |
| 2010/0268069 A1* | 10/2010 | Liang | A61C 9/006 600/425 |

OTHER PUBLICATIONS

Notification of transmittal of International search report PCT/IB2012/050444, Jun. 22, 2012.
International search report PCT/IB2012/050444, Jun. 22, 2012.
Written Opinion of the International Searching Authority, Jun. 22, 2012, PCT/IB2012/050444.
"Differential optical spectropolarimetric imaging system assisted by liquid crystal devices for skin imaging", OFIR AHARON, Journal of Biomedical Optics 16(8), 086008 (Aug. 2011).
Patent Examination Report No. 1, App No. 2012213088, Australian Intellectual Propert Office, Dec. 2, 2014.
Written opinion of the Singapore Intellectual Property Office, Aug. 8, 2014.
New Zealand Intellectual Property Office, First Examination Report, Mar. 11, 2014.
J. Philip, Carter NJ, Lenn CP. "Improved optical discrimination of skin with polarized light". J Soc Cosmet Chem. 1988;39:121-132.
R.R. Anderson, "Polarized light examination and photography of the skin," Arch Dermatol, 127, (1991).
Steven L. Jacques, Jessica C. Ramella-Roman, Ken Lee, "Imaging skin pathology with polarized light," Journal of Biomedical Optics vol. 7, 3 (2002).
Steven L. Jacques and K. Lee, "Polarized video imaging of skin," Proc. SPIE 3245, 356-362 (1998).
Steven L. Jacques, et al. "Imaging Superficial Tissues With Polarized Light," Lasers in Surgery and Medicine 26:119-129 (2000).
R.R. Anderson, "Demarcation of Nonmelanoma Skin Cancer Margins in Thick Excisions Using Multispectral Polarized Light Imaging," The Society for Investigative Dermatology, (2003).
Juan M. Bueno and Pablo Artal , "Double-pass imaging polarimetry in the human eye," Optics Letters / vol. 24, No. 1 / Jan. 1, 1999.
Blandine Laude-Boulesteix, Antonello De Martino, Bernard Dre'villon, and Laurent Schwartz, "Mueller polarimetric imaging system with liquid crystals," Applied Optics, 43, 14 (2004).
Jessica C. Ramella-Roman, "Design, testing, and clinical studies of a handheld polarized light camera," Journal of Biomedical Optics 9(6), 1305-1310 (2004).
Anke Weber, Michael C. Cheney, Quinn Y.J. Smithwick, Ann E. Elsner, "Polarimetric imaging and blood vessel quantification," Optics Express , 12, 21 (2004).
Gang L. Liu, Yanfang Li, and Brent D. Cameron, Polarization-Based Optical Imaging and Processing Techniques with Application to the Cancer Diagnostics, SPIE 4617 (2002).

R. Ramella et al. "Out-of-plane polarimetric imaging of skin: Surface and subsurface effects," Proc. SPIE 5686, 142-153 (2005).
Ramella-Romano,Ken Lee, Scott A. Prahl, Steven L. Jacques, Design, testing, and clinical studies of a handheld polarized light camera, Journal of Biomedical Optics 9(6), 1305-1310 (Nov. Dec. 2004).
Yong-Qiang Zhao, "New polarization imaging method based on spatially adaptive wavelet image fusion," Optical Engineering, 45, 12, (2006).
B. Boulbry, T. A. Germer, and J. C. Ramella-Roman, "A novel hemispherical spectro-polarimetric scattering instrument for skin lesion imaging," Proc. SPIE 6078, 128-134 (2006).
Yong-Qiang Zhao, Lei Zhang, and Quan Pan, "Spectropolarimetric imaging for pathological analysis of skin," 48, 10 pp. (2009).
I. T. Jolliffe, Principal Component Analysis, 2nd ed. (Springer-Verlag, 2002), Chap. 6, pp. 111-130.
G. Pajares and J. Manuel de la Cruz, "A wavelet-based image fusion tutorial," Pattern Recogn. 37, 1855-1872 (2004).
R. Zhang, W. Verkruysse, B. Choi, J. A. Viator, B. Jung, L. O. Svaasand, G. Aguilar and J. S. Nelson, "Determination of human skin optical properties from spectrophotometric measurements based on optimization by genetic algorithms," J.Biomed. Opt. 10(2), 024030 (2005).
C. A. Morton and R. M. Mackie, "Clinical accuracy of the diagnosis of cutaneous malignant melanoma," Br. J. Dermatol. 138(2), 283-287 (1998).
A. M. P. Montgomery, R. A. Reisfeld, and D. A. Cheresh, "Integrin $\alpha v \beta 3$ rescues melanoma cells from apoptosis in three-dimensional dermal collagen," Proc. Natl. Acad. Sci. U.S. A. 91(19), 8856-8860 (1994).
R. R. Anderson and J. A. Parrish, "The optics of human skin," J Invest. Dermatol. 77(1), 13-19 (1981).
V. Backmanv, R. Gurjar, K. Badizadegan, I. Itzkan, R. R. Dasari, L. T. Perelman, and M. S. Feld, "Polarized light scattering spectroscopy for quantitative measurement of epithelial cellular structures in situ," IEEE J. Quantum Electron. 5(4), 1019-1026 (1999).
R. S. Gurjar, V. Backman, L. T. Perelman, L Georgakoudi, K. Badizadegan, I. Itzkan, R. R. Dasari, and M. S. Feld, "Imaging human epithelial properties with polarized light-scattering spectroscopy," Nat. Med. 7(11), 1245-1248 (2001).
R. S. Gurjar, V. Backman, L. T. Perelman, I. Georgakoudi, K. Badizadegan, I. Itzkan, R. R. Dasari, and M. S. Feld, "Imaging human epithelial properties with polarized light-scattering spectroscopy," Nat. Med. 7(11), 1245-1248 (2001).
R. R. Anderson, "Polarized light examination and photography of the skin," Arch. Dermatol. 127(7), 1000-1005 (1991).
A. N. Yaroslavsky, V. Neel, and R. R. Anderson, "Demarcation of nonmelanoma skin cancer margins in thick excisions using multispectral polarized light imaging," J. Investig. Dermatol. 121(2), 259-266 (2003).
B. Laude-Bouleseix, A. De Martino, B. Dr'evillon, and L. Schwartz, "Mueller polarimetric imaging system with liquid crystals," Appl. Opt. 43(14), 2824-2832 (2004).
D. Aharon and I. Abdulhalim, "Liquid crystal Lyot tunable filter with extended free spectral range," Opt. Express 17 (14), 11426-11433 (2009).
D. Aharon and I. Abdulhalim, "Liquid crystal wavelength-independent continuous polarization rotator,"Opt. Eng. 49 (3), 0340021 (2010).
C. Ye, "Construction of an optical rotator using quarter-wave plates and an optical retarder," Opt. Eng. 34(10), 3031-3035 (1995).
Data Sheet, NI DAQCard-6715 High-Speed Analog Output for PCMCIA-12-Bit, 1 MS/s/ch.
I. Abdulhalim, "Dispersion relations for liquid crystals using the anisotropic Lorentz model with geometrical effects," Liq. Cryst. 33(9), 1027-1041 (2006).
D. Aharon, A. Safrani, R. Moses, and I. Abdulhalim, "Liquid crystal tunable filters and polarization controllers for biomedical optical imaging," Proc. SPIE 7050, 70500P (2008).
I. Abdulhalim, R. Moses, and R. Sharon, "Biomedical optical applications of liquid crystal devices," Acta Phys. Polo. A 112(5), 715-722 (2007).

(56) References Cited

OTHER PUBLICATIONS

Letter to Nature, Y. O'Ham, "A new monochromator," Nature (London) 41,157-291 (1938).

A. Lien, "Extended Jones matrix representation for the twisted nematic liquid crystal display at oblique incidence," Appl. Phys. Lett. 57(26), 2767-2770 (1990).

I. Abdulhalim and D. Menashe, "Approximate analytic solutions for the director profile of homogeneously aligned hematic liquid crystals," Liq. Cryst. 37(2), 233-239 (2010).

P. Szab'o, M. Nagy, and T. Vicsek, "Transitions in a self-propelledparticles model with coupling of accelerations," Phys. Rev. E 79(2), 0219081 (2009).

G. Brown, P. A. Rikvold, M. Sutton, and M. Grant, "Evolution of speckle during spinodal decomposition," Phys. Rev. E 60(5), 515151 (1999).

1st office action letter from the State Intellectual Property Office China, Dec. 12, 2014.

2nd office action letter from the State Intellectual Property Office China, Oct. 10, 2015.

Translation of p. 3 of 2nd office action letter from the State Intellectual Property Office China, Oct. 10, 2015.

2nd written opinion of the Intellectual Property Office of Singapore, App No. 2103080049, Feb. 27, 2012.

Certificate of grant, Australian Government, IP Australia, Aug. 6, 2015, App No. 2012213088.

Notice of acceptance and bibliography, Australian Government, IP Australia, Apr. 13, 2015, App No. 2012213088.

Granted application of App No. 2012213088Australian Government, IP Australia, Mar. 25, 2015.

Letter from Columbian Associate TOBOS, conveying the results of the substantial examination of the Colombian Patent Office, Dec. 14, 2015.

First Office Action of Korean patent office, Jul. 24, 2015.

Translation of First Office Action of Korean patent office, Jul. 24, 2015.

Notice of acceptance, Australian Government, IP Australia, May 13, 2015, App No. 2012213088.

Substantiative Examination Report, Intellectual Property Office of the Philippines, Oct. 20, 2105.

* cited by examiner

30

OPTICAL POLARIMETRIC IMAGING

BACKGROUND

1. Technical Field

The present invention is related to probing morphology of tissue, such as in vivo skin tissue in vivo.

2. Description of Related Art

The phenomena of changing polarization state of back scattered light from a turbid medium are well known. In 1988, Philip et al.[2] studied these phenomena in skin tissue and followed by Anderson et al.[3] in 1991. In 1998-2002 Jacques used a side illumination apparatuses.[4,5,6] In 2003, Anderson used his method for skin lesion boundary detection for Mohs micrographic surgery. [7] An enhanced view of vasculature and pigmented lesions was obtained. In 1999, Bueno et al.[8] showed an imaging of the eye retina by extracting the 16 parameters of Mueller matrix. The degree of polarization (DOP) was extracted from those images for the retinal plane. In 2004, Boulesteix et al.[9] used the method for stained hepatic biopsy, extracting the degree of polarization from Mueller matrices at the visible and near infrared spectral realms, and anomalous structure of the collagen was emphasized at different wavelengths. In the same year Ramella et al. [10] simplified the readout of two polarization (parallel and crossed polarizations compared with the light source polarization) from a tissue by using two cameras and calculated the normalized contrast between them simultaneously (S1 parameter of Stokes vector). Weber et al.[11] manipulated the cross and parallel polarizations separately so a tiny vein in the eye could be recognized. Liu et al.[12] measured the backscattering Mueller matrix of a rat-skin sample almost in real-time using side illumination and the diattenuation, retardance and the depolarization parameters were deduced from the Mueller matrices. In 2005 Ramella et al.[13] described a better way to illuminate the tissue by skewed illumination for back scattered imaging and even a handy tool. [14] This allowed them to eliminate the glare with no need for oil or water as matching refractive index. Polarization contrast symbolized by Stokes parameters Pol=S1/S0 carry only few percentages of the light source. Thus in 2006 Zhao et al.[15] removed the noise by using adaptive wavelet transform method that can be easily applied to tissue imaging. Bruno et al.[16] constructed hemispherical spectro-polarimetric scattering instrument to manipulate series of Stokes parameters. In 2009 Zhao et al.[17] harnessed the principal component analysis (PCA) and image fusion[18,19] to the analysis of tissue characteristics and proposed a visual enhancement method to fuse the acquired spectral and polarimetric information by using false color mapping.

U.S. Pat. No. 7,289,211[1] discloses methods for calculating Stokes parameters on reflection from skin tissue.

Zhang et al. [20] performed research on an Asian male with a dark red skin and a Caucasian male with a light-pink skin. As a rule of thumb, these types of skin are the typical among all kinds of skin and surely suitable for spectral decision of preferable wavelengths.

REFERENCES

[1] Joseph T. Wals, "System and method for imaging subsurface polarization-sensitive material structures," U.S. Pat. No. 7,289,211, Issue date: Oct. 30, 2007.

[2] J. Philip, Carter N J, Lenn C P. "Improved optical discrimination of skin with polarized light". J Soc Cosmet Chem. 1988; 39:121-132.

[3] R. R. Anderson, "Polarized light examination and photography of the skin," Arch Dermatol, 127, (1991)

[4] Steven L. Jacques, Jessica C. Ramella-Roman, Ken Lee, "Imaging skin pathology with polarized light," Journal of Biomedical Optics Vol. 7, 3 (2002).

[5] S. L. Jacques and K. Lee, "Polarized video imaging of skin," Proc. SPIE 3245, 356-362 (1998).

[6] Steven L. Jacques, et al. "Imaging Superficial Tissues With Polarized Light," Lasers in Surgery and Medicine 26:119-129 (2000).

[7] R. R. Anderson, "Demarcation of Nonmelanoma Skin Cancer Margins in Thick Excisions Using Multispectral Polarized Light Imaging," The Society for Investigative Dermatology, (2003)

[8] Juan M. Bueno and Pablo Artal, "Double-pass imaging polarimetry in the human eye," OPTICS LETTERS/Vol. 24, No. 1/Jan. 1, 1999.

[9] Blandine Laude-Boulesteix, Antonello De Martino, Bernard Dre'villon, and Laurent Schwartz, "Mueller polarimetric imaging system with liquid crystals," APPLIED OPTICS, 43, 14 (2004).

[10] Jessica C. Ramella-Roman, "Design, testing, and clinical studies of a handheld polarized light camera," Journal of Biomedical Optics 9(6), 1305-1310 (2004).

[11] Anke Weber, Michael C. Cheney, Quinn Y. J. Smithwick, Ann E. Elsner, "Polarimetric imaging and blood vessel quantification," OPTICS EXPRESS, 12, 21 (2004).

[12] Gang L. Liu, Yanfang Li, and Brent D. Cameron, Polarization-Based Optical Imaging and Processing Techniques with Application to the Cancer Diagnostics," SPIE 4617 (2002).

[13] R. Ramella et al. "Out-of-plane polarimetric imaging of skin: Surface and subsurface effects," Proc. SPIE 5686, 142-153 (2005).

[14] Ramella-Romano, Ken Lee, Scott A. Prahl, Steven L. Jacques, Design, testing, and clinical studies of a handheld polarized light camera, Journal of Biomedical Optics 9(6), 1305-1310 (NovemberDecember 2004)

[15] Yong-Qiang Zhao, "New polarization imaging method based on spatially adaptive wavelet image fusion," Optical Engineering, 45, 12, (2006).

[16] B. Boulbry, T. A. Germer, and J. C. Ramella-Roman, "A novel hemispherical spectro-polarimetric scattering instrument for skin lesion imaging," Proc. SPIE 6078, 128-134 (2006).

[17]. Yongqiang Zhao, Lei Zhang, and Quan Pan, "Spectropolarimetric imaging for pathological analysis of skin," 48, 10 pp. (2009).

[18] I. T. Jolliffe, Principal Component Analysis, 2nd ed. (Springer-Verlag, 2002), Chap. 6, pp. 111-130.

[19] G. Pajares and J. Manuel de la Cruz, "A wavelet-based image fusion tutorial," Pattern Recogn. 37, 1855-1872 (2004).

[20]. R. Zhang, W. Verkruysse, B. Choi, J. A. Viator, B. Jung, L. O. Svaasand, G. Aguilar and J. S. Nelson, "Determination of human skin optical properties from spectrophotometric measurements based on optimization by genetic algorithms," J. Biomed. Opt. 10(2), 024030 (2005).

BRIEF SUMMARY

According to features of the present invention, there is provided a method for probing morphology of a tissue surface using a system which may include a light source, a polarizer, an analyzer, and a camera with multiple picture elements. The method illuminates the tissue surface with incident light through the polarizer. The illumination may be performed for incident light of different spectral content. The camera may capture through the analyzer, scattered light from the tissue surface in a continuous sequence of image frames. Variation of polarization state may be of at least one of (1) the incident light from the light source by varying the polarizer or (2) the scattered light from the tissue surface by varying the analyzer. During the capture, for a picture element of the camera, a varying intensity signal of the scattered light is detected responsive to the varying polarization state. The varying intensity signal may be a periodic intensity signal. The varying intensity signal may be analyzed for at least one of the picture elements throughout the image frames to probe the morphology of the tissue surface. The analysis may include determination of light intensity contrast between peaks and troughs of the varying intensity signal. The analysis may include determination of an intensity differential of the varying intensity signal between image frames. The analysis may include the determination of an intensity differential of the varying intensity signal between consecutive image frames. The analysis may include the determination of a second or higher derivative of the varying intensity signal between the image frames. The varying intensity signal may be a function of time and the analysis may include performing a transform of the varying intensity signal to a transformed intensity signal in frequency domain. The analysis may include the determination of an average of contrasts between frames of the varying intensity signal. The analysis may include determination of a variance of the varying intensity signal.

According to features of the present invention, there is provided a system including a light source, a variable polarizer, a second polarizer, and a camera including an image sensor with a plurality of picture elements. The system may be operable to illuminate the tissue surface with incident light through the polarizer. Scattered light is captured by the camera through the analyzer from the tissue surface in a continuous sequence of image frames. Polarization state is varied of at least one of (1) the incident light from the light source (2) the scattered light from the tissue surface. A varying intensity signal of the scattered light is detected responsive to the varying polarization state. The varying intensity signal may be a periodic intensity signal. The varying intensity signal may be a periodic intensity signal. An analysis of the varying intensity signal is performed for at least one of the picture elements throughout the image frames to probe the morphology of the tissue surface. The analysis of the varying intensity signal may include a light intensity contrast between peaks and troughs of the varying intensity signal. The analysis of the varying intensity signal may include an intensity differential of the varying signal between image frames. The analysis of the varying intensity signal may include a second derivative of the varying intensity signal between the image frames. The analysis of the varying intensity signal may include an average intensity of contrasts between frames of the varying intensity signal. The analysis of the varying intensity signal may include a variance of the varying intensity signal. The varying intensity signal may be a function of time and the analysis of the varying intensity signal may perform a transform of the varying intensity signal to a transformed intensity signal in frequency domain. The system may further include a mechanism for varying spectral content of the incident light.

BRIEF DESCRIPTION OF THE DRAWINGS

The invention is herein described, by way of example only, with reference to the accompanying drawings, wherein.

DETAILED DESCRIPTION

Figure 1A:
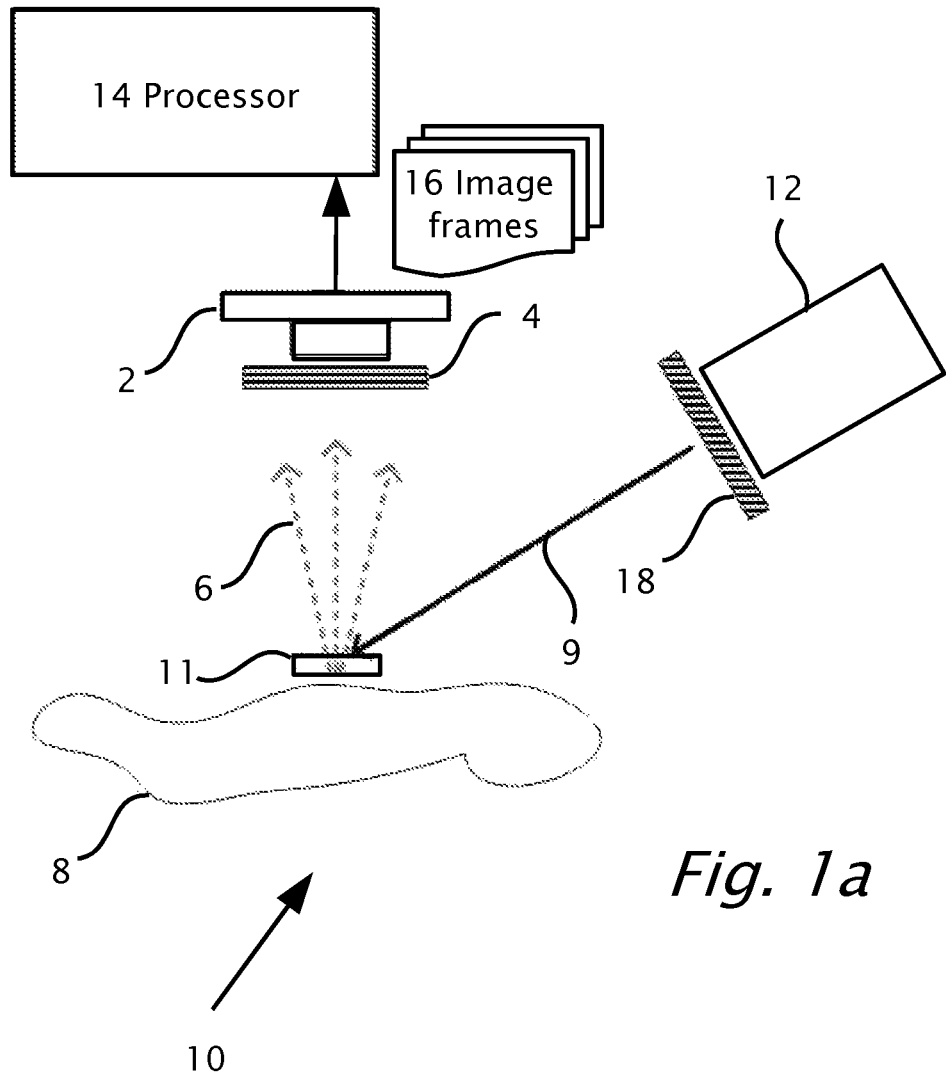
FIG. 1a shows a system diagram for probing morphology of a tissue surface, according to a feature of the present invention.

Reference will now be made in detail to features of the present invention, examples of which are illustrated in the accompanying drawings, wherein like reference numerals refer to the like elements throughout. The features are described below to explain the present invention by referring to the figures.

Before explaining features of the invention in detail, it is to be understood that the invention is not limited in its application to the details of design and the arrangement of the components set forth in the following description or illustrated in the drawings. The invention is capable of other features or of being practiced or carried out in various ways. Also, it is to be understood that the phraseology and terminology employed herein is for the purpose of description and should not be regarded as limiting.

By way of introduction aspects of the present invention are directed to novel methods for probing tissue such as skin tissue. In the methods disclosed herein, Stokes parameters or Mueller matrix parameters are not explicitly determined. The polarization state of the light incident on the surface being probed is varied for instance periodically. The scattered light is viewed by a camera through an analyzer. A sequence of image frames are obtained of the scattered light while the incident or scattered light polarization is being varied. Varying, (typically periodic) intensity signals of scattered light are produced for one or more picture elements of the camera. Processing of the image frames and the intensity signals may be performed in several ways according to different aspects of the present invention. For instance, the sequence of image frames may be used to extract the average contrast between adjacent image frames. The sequence of the image frames may be used to extract the scattered light intensity differential at one or more nearby picture elements from image frame to image frame. Similar, higher order derivatives of the intensity variation may be determined for one or more pixels from image frame to image frame.

The methods as disclosed herein may be applied to diagnose skin lesions.

The terms "polarizer" and "analyzer" are used herein to refer to one or more polarizing optical elements which operate by refraction, reflection, absorption and/or diffraction including one or more birefringent waveplates and/or electro-optic devices.

The term "average" or "mean" as used herein refers to an average value of a set of light intensity values. The average is calculated by combining the light intensity values from the list in a specific way, e.g. adding, and computing a single number as being the average of the list e.g., by dividing by the number of light intensity values in list.

The term "variance" as used herein refers to a measure of how far a set of light intensity values are spread out. Variance is one of several descriptors of a probability distribution describing how far the set of light intensity values are from the average light intensity value. In particular, the variance may be one of the moments of the probability distribution. Variance may be the expected value of the squared difference between measured light intensity and the average of the light intensity.

Reference is now made to FIG. 1a which shows a system diagram 10 for probing morphology of a tissue surface, according to a feature of the present invention. System 10 includes a light source 12 with optics to direct, e.g. collimate, light emitted from light source 12 onto a surface 8, e.g. skin lesion, being probed. The light emitted from light source 12 passes through a polarizer 18 which may continuously and/or periodically changes the polarization state of the light emitted from light source 12 to transmit variable polarized incident light 9 onto surface 8. Light scattered from surface 8 passes through an analyzer 4 and is received by an image sensor or camera 2. Alternatively, or in addition to the incident light, the polarization of scattered light may be varied continuously and/or periodically by for instance rotating analyzer 4. Camera 2 may be a charge coupled device (CCD) or complimentary metal oxide semiconductor CMOS type etc. Camera 2 is connected to processor 14 which receives captured image frames 16 from camera 2. A transparent window 11 may be used to contact tissue surface 8 and incident and scattered light are transmitted through window 11.

Variable polarization of incident light 9 or scattered light 6 may be achieved in any way known in the arts of optics and electro-optics. Polarization may be varied by rotating a birefringent wave plate. Other devices used to vary incident or scattered light polarization may include use of spatial modulation, e.g. liquid crystal polarization modulator. The polarization of incident light 9 may be varied from linear to circular or circular to linear. The angle of linearly polarized light or elliptically polarized light may be varied. One state of elliptical polarization may be varied to any other state of polarization. Any change in the Stokes parameters or Mueller parameters may be represented in incident light 9.

Varying polarization state may be performed by varying polarization state for instance by rotation, of polarizer 18 and/or of analyzer 4. Polarization of incident light 9 may be changing while analyzer 4 in front of camera 2 is fixed. Polarizer 18 of incident light 9 may be fixed and analyzer 4 in front of camera 2 may be changing, e.g. rotating. Polarizer 18 and analyzer 4 may both be changing, e.g. rotating at the same time.

In all cases, camera 2 captures a sequence of image frames 16 during the varying polarization.

If surface 8 has monotonic optical morphology, scattered light 6 may not experience significant change while polarization is varied. Boundaries and high scattering zones may be more sensitive to changes in the polarization of incident light 9 and may produce different images for different incident polarization states.

Figures 1B, 1C:
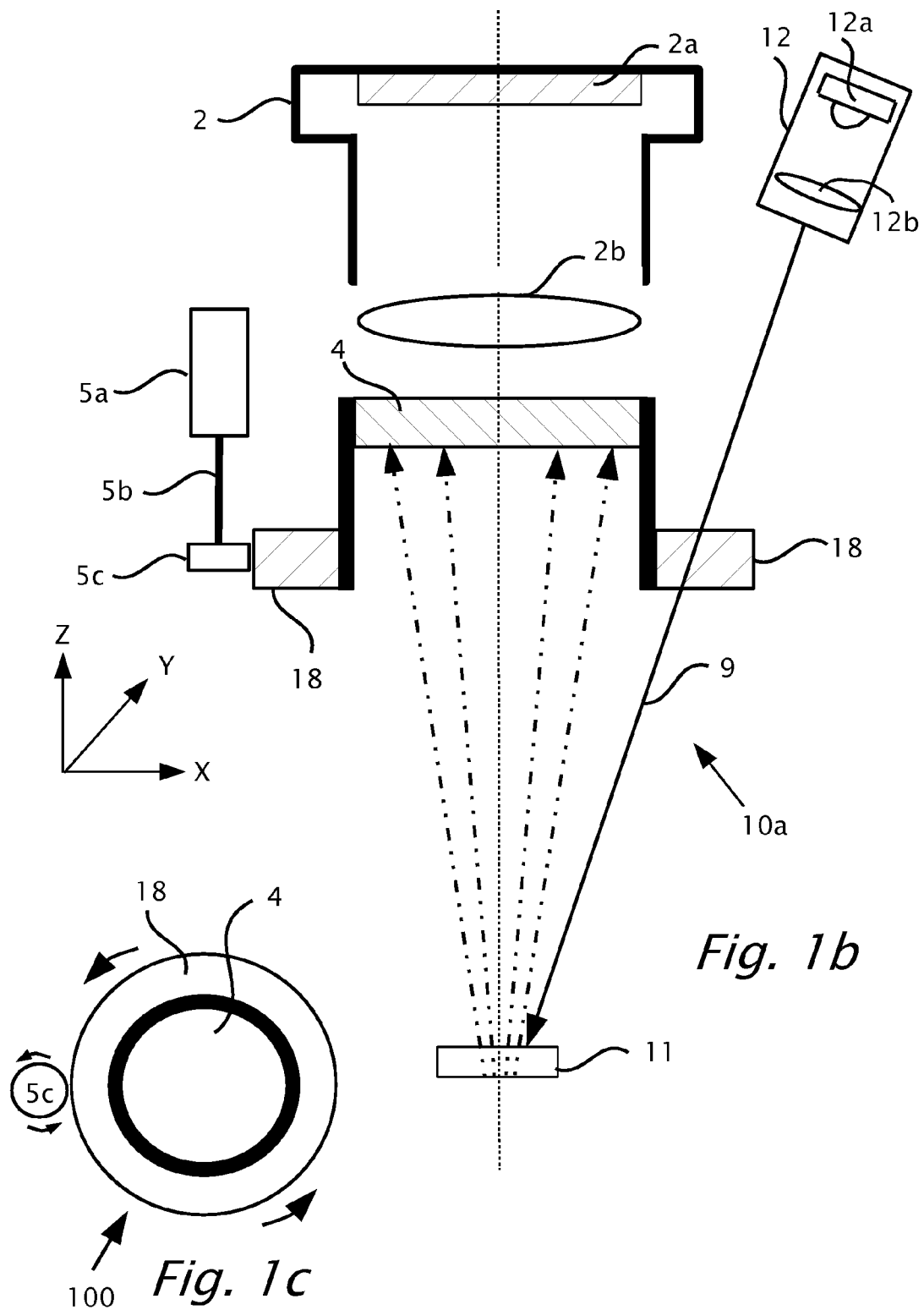
FIGS. 1b and 1c show a cross section view and a plan view respectively of an implementation of system components found in the system shown in FIG. 1a, according to an exemplary feature.

Reference is now made to FIGS. 1b and 1c which show a cross section view 10a and a plan view 100 respectively of an implementation of system components found in system 10 shown in FIG. 1a, according to an exemplary feature. Camera 2 is shown with image sensor 2a and lens 2b. With sensor 2a and lens 2b perpendicular to the Z axis are analyzer 4, polarizer 18 and window 11. A motor 5a with drive shaft 5b is connected to cog wheel 5c. Cog wheel when rotated by motor 5a rotates polarizer 18 in a direction at right angles to the Z axis. Light source 12 may include a lamp 12a and lens 12b. The focused light emitted from light source 12 goes through polarizer 18 to transmit variable polarized incident light 9 onto window 11 and/or surface 8 by virtue of the rotation of polarizer 18. Scattered light from window 11 and/or surface 8 goes through stationary analyzer 4, through lens 2b and onto image sensor 2a.

Figure 1D:
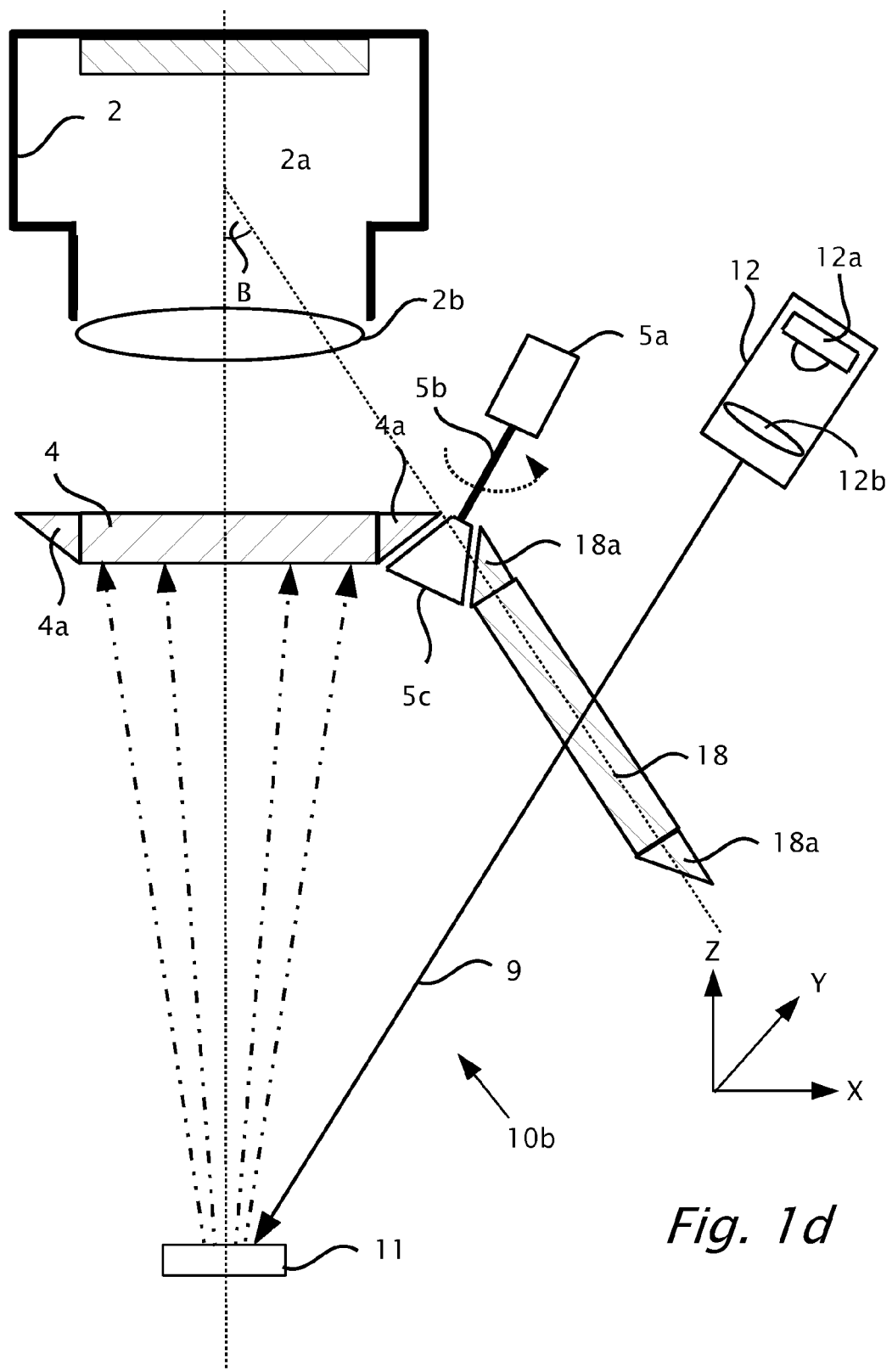
FIG. 1d shows a cross section view of an implementation of system components found in the system shown in FIG. 1a, according to another exemplary feature.

Reference is now made to FIG. 1d which shows a cross section view 10b and of an implementation of system components found in system 10 shown in FIG. 1a, according to another exemplary feature. Cog wheel 5c when rotated by motor 5a rotates polarizer 18 and analyzer 4 by virtue of angular components 18a and 4a attached to polarizer 18 and analyzer 4 respectively. Analyzer 4 rotates in a plane which is at right angles to the Z axis and polarizer 18 rotates in a plane at an angle B relative to the Z axis. Angle B may be and less than ninety degrees. The focused light emitted from light source 12 goes through polarizer 18 to transmit variable polarized incident light 9 onto window 11 and/or surface 8 by virtue of the rotation of polarizer 18. Scattered light from window 11 and/or surface 8 goes through analyzer 4 which is also rotating, through lens 2b and onto image sensor 2a.

Figure 1E:
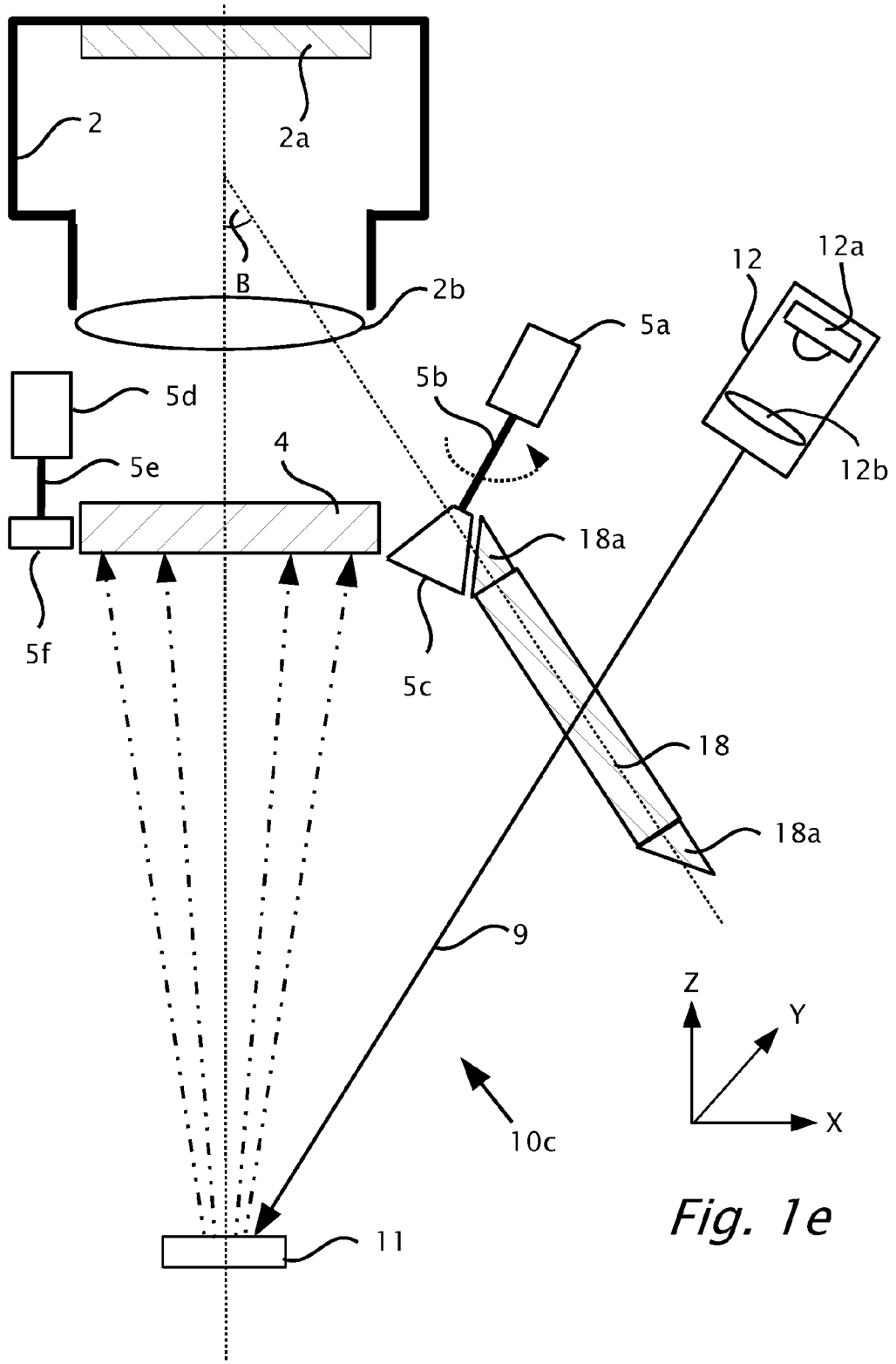
FIG. 1e shows a cross section view of an implementation of system components found in the system shown in FIG. 1a, according to yet another exemplary feature.

Reference is now made to FIG. 1e which shows a cross section view 10c and of an implementation of system components found in system 10 shown in FIG. 1a, according to yet another exemplary feature. FIGS. 1e and 1d are similar except two motors 5a and 5d respectively, which rotate polarizer 18 and analyzer 4 independently from each other. cog wheel 5c attached to drive shaft 5b and motor 5a, connects with angular component 18a of polarizer 18 so as to rotate polarizer 18. Similarly cog wheel 5f attached to drive shaft 5e and motor 5d, connects with analyzer 4 so as to rotate polarizer 4.

Pre-Processing of the Captured Video Sequence

A skin lesion is a good example due to scattering in its epidermal layers. The captured sequence can be processed as separate files of image frames 16, or the sequence may also optionally be processed as a video sequence in a single file. System 10 may be applied to image skin lesions, while the angle of linearly polarized light is changed by rotating polarizer 18. Scattered light scatters upward toward camera 2. Camera 2 captures frames 16 as shown schematically in FIG. 2a. Image frames 16 have indices k=1 to N, $I_k$ is the $k^{th}$ frame among N frames. Polarizer 18 may be rotated multiple times to improve signal to noise in algorithms. Each frame $I_k$, of e.g.

640×480 picture elements (pixels) in current examples corresponds substantially to a single state of polarization angle-$\alpha_k$ produced by polarizer 18.

Figure 2:
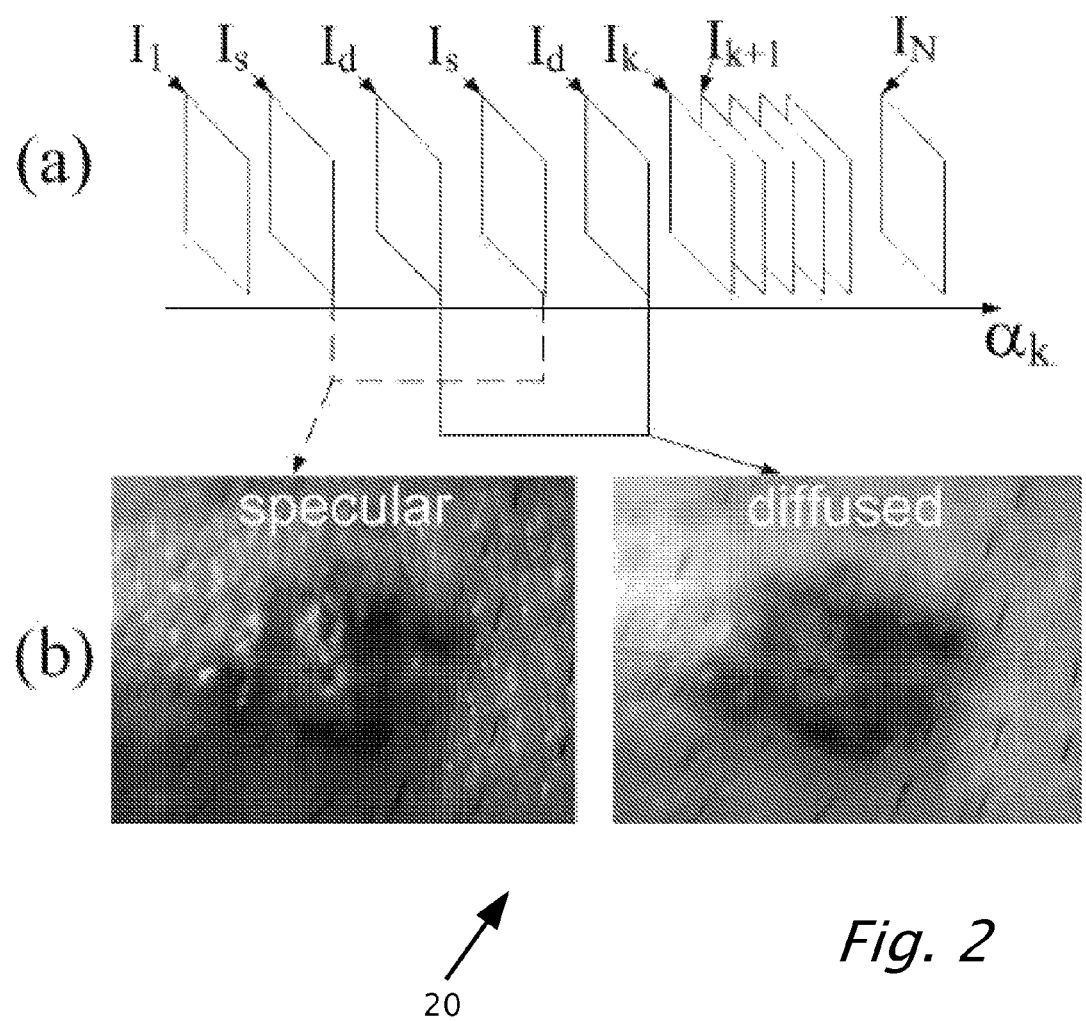
FIG. 2a shows a series of captured image frames according to an feature of the present invention.
FIG. 2b shows two examples of $I_s$ and $I_d$ of basal cell carcinoma.

Reference is now made to FIG. 2 which illustrates schematically a sequence of image frames 16 captured at different incident polarization states of a skin lesion. N frames are taken during continuous change in polarization state $\alpha_k$. $I_s$ is shown as the image frame 16 when a prominent specular-like image appears. $I_d$ is shown when the image appears diffuse and non-specular. The images labelled "specular" and "diffused" are for a basal cell carcinoma (BCC).

Methods disclosed herein using skin lesion surface 8 as a non-limiting example of tissue or scattering material; however the method may optionally be applied to any other semi-transparent surface.

During variations in polarizer 18, the scattered light 6 from the lesion is also change due to scattering from hetro-structures inside the skin. Areas which have no variation in their structure will not produce significant differences in the scattered light 6, hence, the captured image frames 16 may show minimal change from frame to frame. More significant differences are expected between image frames 16 when material boundaries or scattering sites are present. In this case, scattered light 6 may change its polarization and intensity for each state of polarization of the incident light. To uncover these structural variations in the material index of refraction or in general—optical morphology, different algorithms are optionally used to emphasize boundaries and degree of scattered light 6 over the surface being probed.

1) Specular-Diffuse Algorithm, SD algorithm.
2) Average Frame Contrast, named AFC algorithm.
3) Averaged Differential algorithm, named AD2 algorithm, when applied for the $2^{nd}$ order of differentiation.
    NOTE: AD3, AD4 . . . ADn (n=integer), may be applied for higher orders of differentiation.

SD Algorithm: Specular-Diffused

Among the whole sequence of image frames 16 a specular-like reflection may be seen clearly from the superficial layer of the inspected surface. In skin, it would be the stratum corneum. Specular-like image frames 16 are marked as $I_s$ in FIG. 2, where s stands for specular-like signatures (bright surface) usually happen when the incident polarization is at the same polarization as analyzer 4. Between the $I_s$ image frames 16 there are the diffusive image frames 16 $I_d$ which usually happen when the polarization of the surface reflection and analyzer 4 are orthogonal. FIG. 2b shows two examples of $I_s$ and $I_d$ of basal cell carcinoma. It can be seen that $I_s$ image frame 16 has more glare on its surface and $I_d$ is lack of this glare. In a similar manner to the definition of the normalized second Stokes parameter one may define the following SD image designating the contrast between the specular-like $I_s$ image frame 16 and diffusive $I_d$ image frames 16:

$$SD=(I_s-I_d)/(I_s+I_d) \quad (1)$$

SD image is different than the second Stokes parameter when the polarizer at camera 2 is fixed and the glare in $I_s$ can be from arbitrary reflection angle. Eq. 1 enables to emphasize boundaries of different scattering zones.

Figure 3:
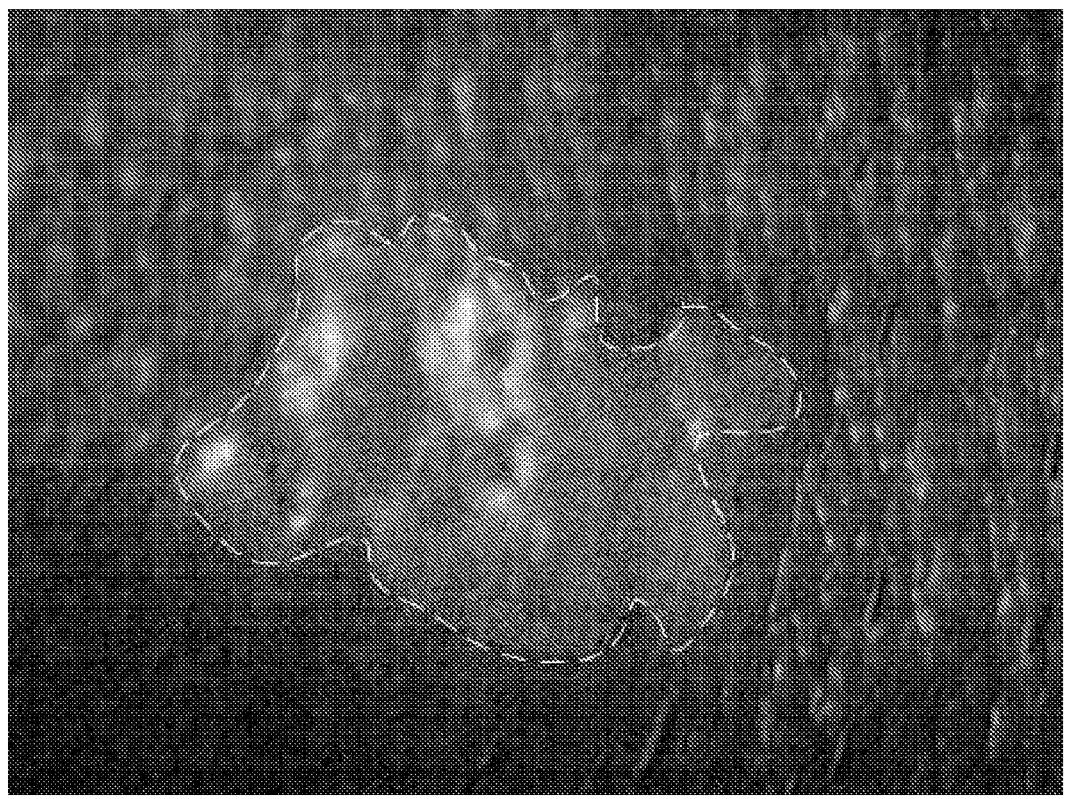
FIG. 3 shows an example of such an SD image using the image frames $I_s$ and $I_d$ shown in FIG. 2b, illustrating a well defined boundary of the basal cell carcinoma.
Figure 3:

FIG. 3 shows an example of such an SD image using the image frames 16 $I_s$ and $I_d$ shown in FIG. 2b, illustrating a well defined boundary of the basal cell carcinoma.

AFC Algorithm: Average Frame Contrast

The optical morphology of surface such as skin lesion has arbitrary optical characteristics of absorption, transmission, scattering and will always be different from lesion to lesion, different areas in the body or for different people. Thus, AFC algorithm takes the average of all contrasts of two adjacent image frames 16 $I_{k+m}$ and $I_k$. m is an integer number, to be chosen by the user, here m=2. Equation (2) demonstrates the contrast between two adjacent states. High spatial change in morphology like scattering areas will produce larger values in $C_k$ images. Recalling the random optical morphology, $C_k$'s will be averaged in the final post process as AFC image, defined in Eq. 3.

$$C_k = \frac{|I_{k+2} - I_k|}{I_{k+2} + I_k} \quad (2)$$

$$AFC = \frac{1}{N-1} \sum_{k=1}^{N} C_k \quad (3)$$

AFC algorithm emphasizes the spatial inner changes of high scattering areas over the inspected surface. In skin lesions it can indicate about abnormalities, for instance dysplasia emergence, which can lead to malignancy.

AD2 Algorithm: Averaged Differential of the $2^{nd}$ Degree

Assuming that a surface has high optical scattering, changing the polarization will seldom produce linear change in the recorded intensity of camera 12. Intensity (or image frame 16) recorded by camera 12 will generate a curvature at each pixel during the change in the polarization state. The degree of this curvature is represented by AD2 algorithm in Eq. 4, averaging the differential of the $2^{nd}$ degree for each pixel on camera 2 detector. The higher the curvature the higher the value of AD2.

$$AD2 = \frac{1}{2(N-1)} \sum_{k=1}^{N} |I_{k+2} - I_k| \times |I_{k+2} + I_k - 2I_{k+1}| \quad (4)$$

$|I_{k+2}+I_k-2I_{k+1}|$ is related to the numerical second derivation and indicates about the degree of curvature of the change in intensity $I_k$.

In order to avoid cases where the change between two points $I_{k+2}$ and $I_k$ is not prominent or originating from noise, $|I_{k+2}+I_k+2I_{k+1}|$ imultiplied by the difference $|I_{k+2}-I_k|$. Eq. 4 can also be written using normalizations by dividing with sum of subtracted elements at the denominator, Eq. 5-7, or just averaging the second derivative as in Eq. 8. Then the image color map will have to be modified. The brackets $(AD2)_1, \ldots (AD2)_4$ indicates the several options to define AD2.

$$(AD2)_1 = \frac{1}{2(N-1)} \sum_{k=1}^{N} \frac{|I_{k+2} - I_k| \times |I_{k+2} + I_k - 2I_{k+1}|}{|I_{k+2} + I_k| \times |I_{k+2} + I_k + 2I_{k+1}|} \quad (5)$$

$$(AD2)_2 = \frac{1}{2(N-1)} \sum_{k=1}^{N} \frac{|I_{k+2} - I_k| \times |I_{k+2} + I_k - 2I_{k+1}|}{|I_{k+2} + I_k + 2I_{k+1}|} \quad (6)$$

$$(AD2)_3 = \frac{1}{2(N-1)} \sum_{k=1}^{N} \frac{|I_{k+2} - I_k| \times |I_{k+2} + I_k - 2I_{k+1}|}{|I_{k+2} + I_k|} \quad (7)$$

$$(AD2)_4 = \frac{1}{2(N-1)} \sum_{k=1}^{N} |I_{k+2} + I_k - 2I_{k+1}| \quad (8)$$

Figure 4:
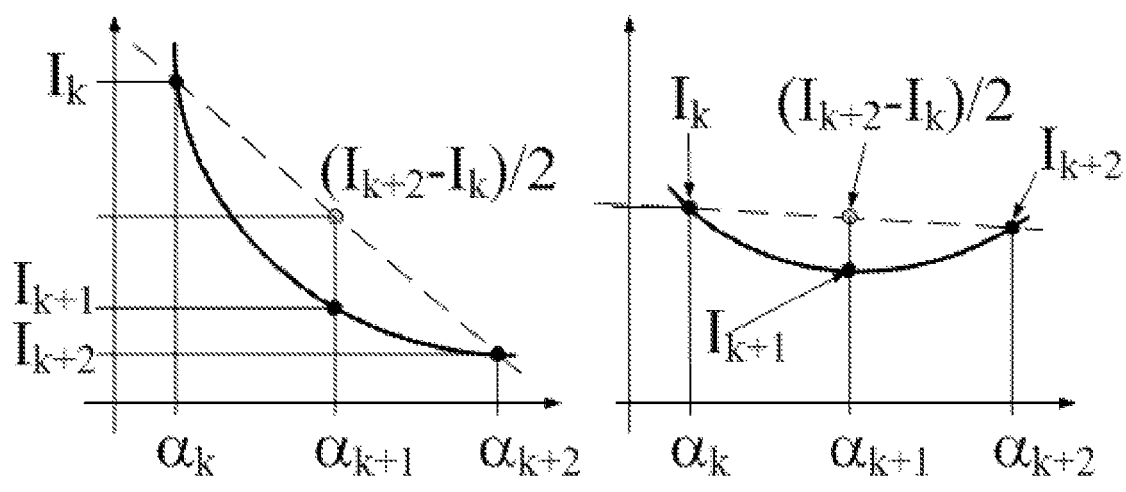
FIGS. 4a and 4b show the sampled signal on one of the camera's pixels.

To understand the meaning of AD2 let us follow the sampled signal on one of the camera's pixels, as shown in FIGS. 4a and 4b, where the axes are the intensity on a particular pixel versus the discrete polarization angle $\alpha_k$ of the incident light on a skin lesion. Numerical curvature measuring can expressed as the magnitude of distance between sampled intensity of the measurement at point $\{\alpha_{k+1}, I_{k+1}\}$, and average value between two adjacent points $I_k$ and $I_{k+2}$, $\{\alpha_{k+1}, (I_{k+2}+I_k)/2\}$. Distance between these two points would be $|(I_{k+2}+I_k)/2-I_{k+1}|$. Note, in Eq.4-8 the division by 2 was taken out of the summary sign.

During the scan the angle of the incident polarization on the lesion changes continuously—hence we expect a continuous change on camera 2 as well, so if $I_{k+2}$ image frame 16 does not change much compared to $I_k$, we interpret the jump in $I_{k+1}$ as a noise and can be ignored and AD2 should be close to the dark level means $I_{k+2}$ and $I_k$ are close to each other.

Reference in now also made to FIGS. 4(a) and 4(b). FIG. 4(a) shows a change in intensity of an arbitrary pixel in camera 2 while a changes. The solid line is the analog intensity, the black circles are its numerical samples. Figure (b) shows a case where there is practically no prominent change between $I_k$ and $I_{k+2}$ where $I_{k+1}$ doesn't lay on the dashed line. In this case $I_{k+1}$ can be considered as a noise.

The graph of FIG. 4b takes into account the multiplication of $|I_{k+2}-I_k|$ in Eq. 4. In other words, Eq. 4 collects cases similar to FIG. 4a when there is a prominent difference between $I_k$, and $I_{k+2}$ which is enforced with the magnitude of the intensity difference between points $I_k$, and $I_{k+2}$). The differential polarization scanning method may consider the fact that deep layers will cause the incident polarized light to lose its polarization and emerge as a non-polarized background light. So equations 3-8 mainly emphasize the changes of the superficial layer of the lesion, while still some degree of polarization is preserved.

Examples

Using Methods as Disclosed Herein in a Clinic

Clinical in vivo images were obtained in Soroka Hospital, Beer-Sheva Israel. Images of skin lesions have been captured before the patients entered into the operation room for their surgery. The following section presents post processing images of AFC and AD2 algorithms using two wavelength 520 nm and 700 nm. Different wavelengths may be applied for different penetration, based on properties that can inferred from the work of Zhang et al. [20]:

(1) large difference between the transmittance at 520 nm and 700 nm and
(2) the spectral dependence around each of these wavelengths is nearly flat.

Figure 5:
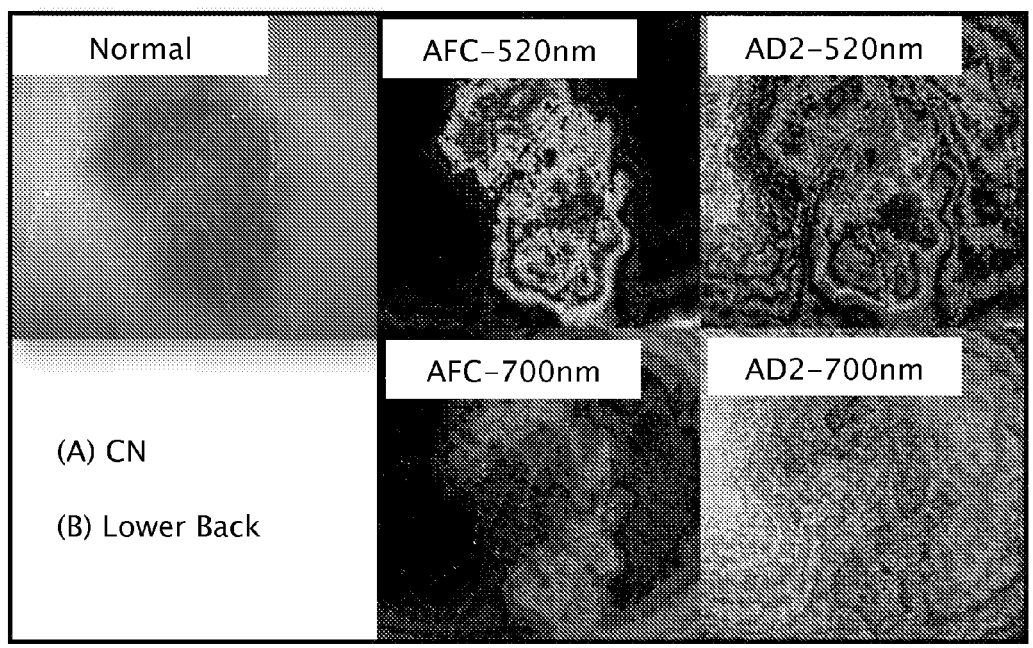
FIG. 5 shows an image of a lesion type—compound nevus (CN), with imaging of compound nevu.

Reference is now also made to FIG. 5 which shows an image of a lesion type—compound nevus (CN), with imaging of compound nevu. As shown in FIG. 5, patterns concealed from the naked eye (FIG. 5-Normal image frame) can be seen very clearly using algorithms AFC and AD2. AFC refers to areas with higher scattering characteristics than the surrounding of the lesion and AD2 indicates on the curvature of the change in the back-scattering. Both cases reveal the tendency of the lesion to become neoplastic.

Figure 6:
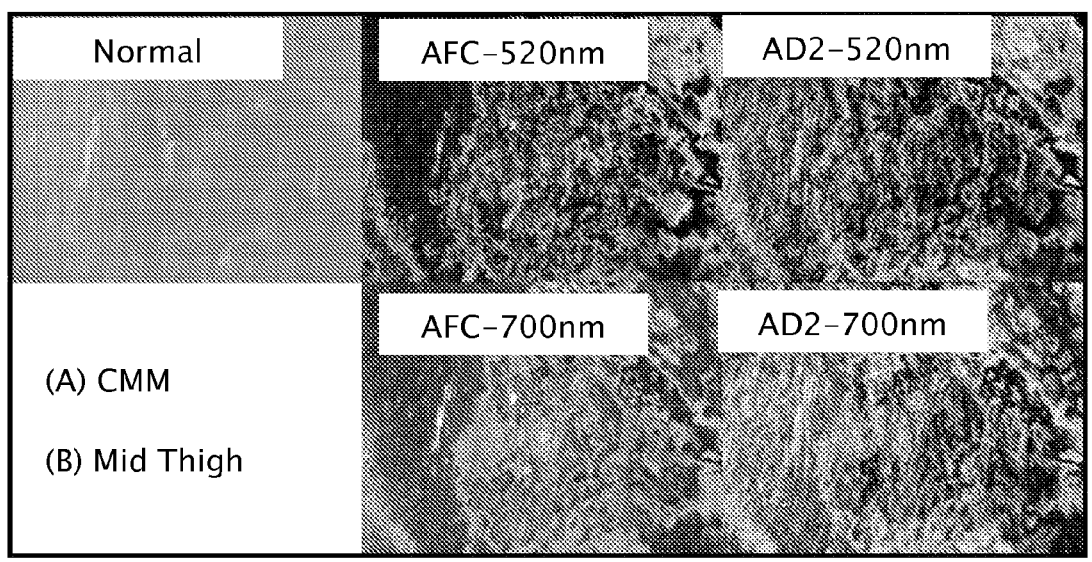
FIG. 6 illustrates a second example of very hard cutaneous malignant melanoma (CMM).

Reference is now made to FIG. 6 which illustrates a second example of very hard cutaneous malignant melanoma (CMM). In this example, the collagen and elastin structures are already damaged and therefore generate random areas of high scattering regions, shaped as islands.

Algorithms, SD, AFC and AD2 enable to distinguish between different degrees of scattered light 6 light from a surface. SD algorithm is mainly used for recognizing lesion's boundary. Monotonic surface appears in AFC and AD2 images as hazy or smeared images, in which variations in surface optical properties appear with patterns alluding to inner structure of the first surface layers, depending on the wavelength. The penetration depth governed by the incident wavelength is a debate of light and matter interaction, in most of the turbid media deep layers will cause the impinged polarized light to lose its polarization and emerges from the surface as background light.

Algorithms may be applied not just for skin lesions but also to any other scattering or turbid medium. The change in captured image frames 16 by camera 2 can be generated in several ways: (1) variations in polarization at the light source or in front of camera 2 (2) changing wavelengths (3) changing light intensity (4) changing apparatus geometry (5) changing light path (6) or any other system parameter resulting change in the captured image frame 16 by camera 2.

Figure 7:
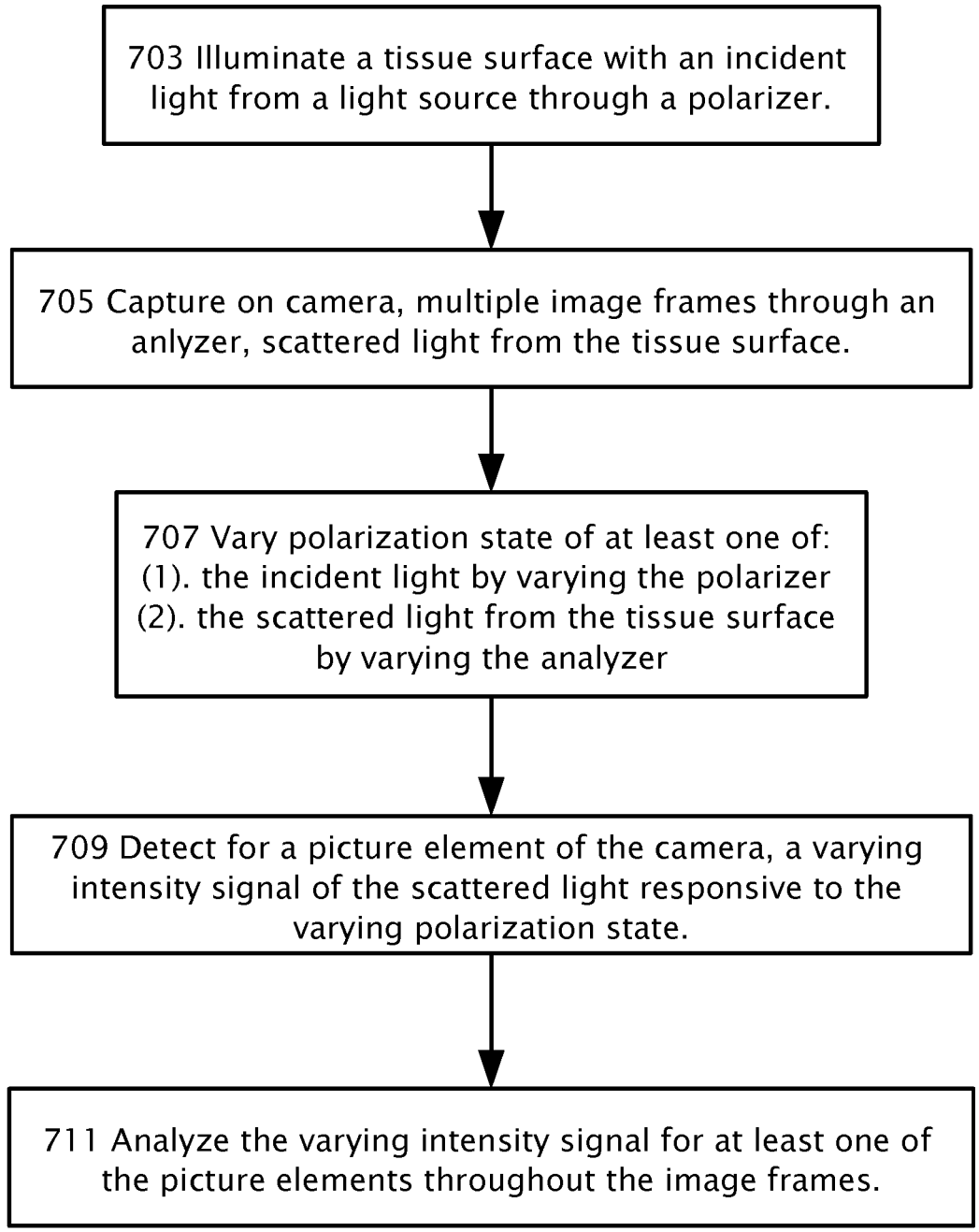
FIG. 7 which shows a method, according to a feature of the present invention.

Reference is now made to FIG. 7 which shows a method 701, according to a feature of the present invention. With window 11 placed on a tissue surface 8, and in step 703, the tissue surface 8 is illuminated through window 11 with polarized incident light 9. Polarized incident light 9 comes from light source 12 through polarizer 18. The scattered light from tissue surface 8 in step 705, transmits through analyzer 4 and into camera 2, through lens 2b and onto image sensor 2a. Camera 2 is operatively attached to processor 14 and multiple image frames 16 are captured and processed by processor 14. As discussed previously, polarizer 18 may be fixed, move together with analyzer 4 or move independently of analyzer 4. Similarly, analyzer 4 may be fixed, move together with polarizer 18 or move independently of polarizer 18. Therefore in step 707, the polarization state may be varied for at least one case of the incident light 9 by varying polarizer 18 or in another case where the scattered light from surface 8 is varied by varying analyzer 4. In step 709 a picture element of camera 2 may be detected which gives a varying intensity signal which is responsive to the polarization state being varied (step 707). In step 711 the varying intensity signal may be analyzed for at least one of the picture elements throughout the image frames 16.

Analysis step 711 may include the determination of an intensity differential or a second differential of the varying intensity signal between image frames 16 or between consecutive image frames 16. Analysis step 711 may further include determination of an average of contrasts between frames of the varying intensity signal and/or a variance of the varying intensity signal. If the varying intensity signal is a function of time, the analyzing step 711 may include a transform of the varying intensity signal to a transformed intensity signal in frequency domain. The transform form may be a fast Fourier transform, Laplace transform or any transform known in the art of signal processing.

Figure 8A:
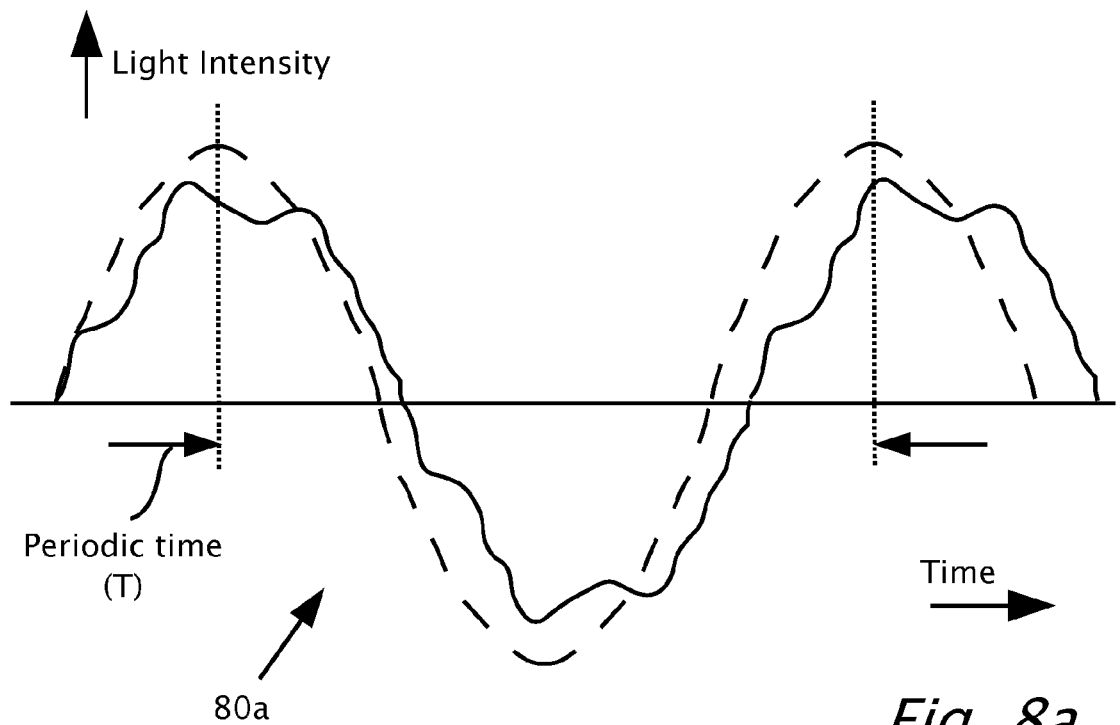
FIGS. 8a and 8b show respective time and frequency domains of a varying light intensity signal.
Figure 8B:
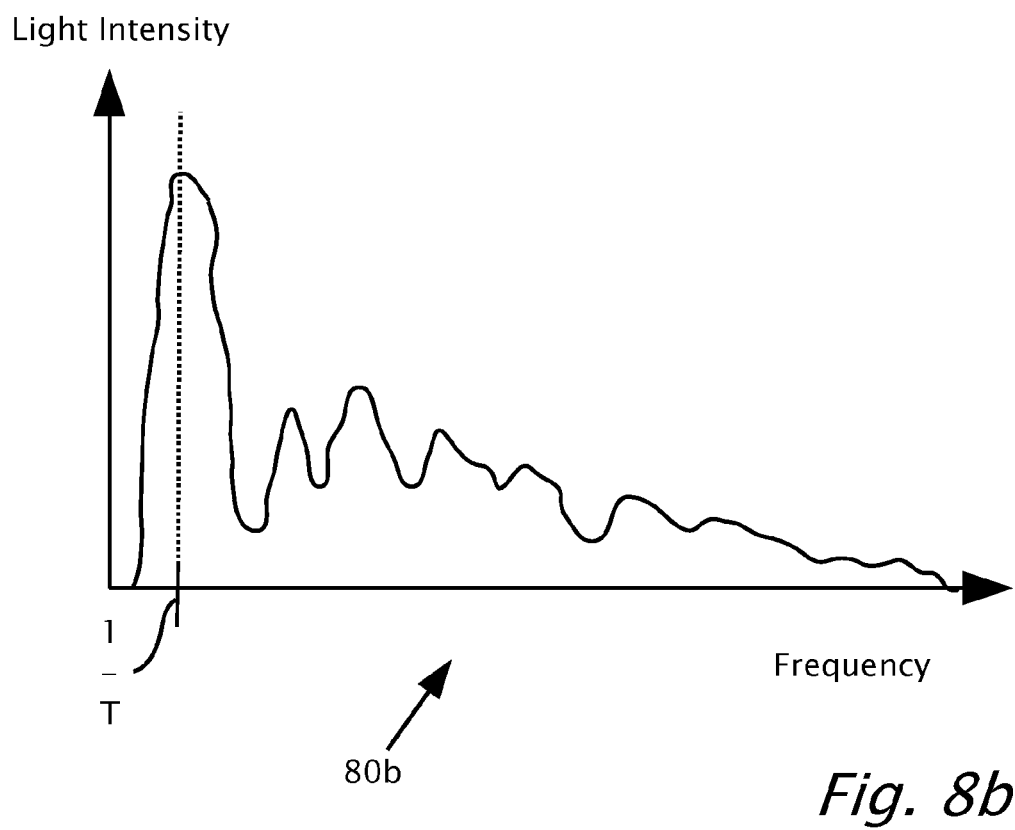

Making reference now to FIGS. 8a and 8b which show respective time 80a and frequency 80b domains of a varying light intensity signal. In FIG. 8a, a dotted line shows a sine wave of time period T and the actual measured amplitude time varying light intensity signal. The frequency domain 80b shows a peak amplitude at a frequency of 1 divided by time period T. Analyzing step 711 in this case may include a determination of light intensity contrast between peaks and troughs of the varying intensity signal shown in tome domain 80a. The frequency domain 80b shows that the varying intensity signal is a periodic intensity signal with a fundamental peak as shown by the peak at a frequency of 1 divided by time period T. The fundamental peak may be indicative of analyzer 4 being in a fixed position and polarizer 18 rotating periodically or vice versa. Two fundamental peaks at two different frequencies may be indicative of both polarizer 18 and analyzer 4 rotating at two different constant velocities. The frequency domain 80*b* shows as well, other frequency components which may be indicative of a particular condition of the tissue surface 8.

The indefinite articles "a", "an" is used herein, such as "a polarizer", "a light source" have the meaning of "one or more" that is "one or more polarizers" or "one or more light sources".

Although selected features of the present invention have been shown and described, it is to be understood the present invention is not limited to the described features. Instead, it is to be appreciated that changes may be made to these features without departing from the principles and spirit of the invention, the scope of which is defined by the claims and the equivalents thereof.

The invention claimed is:

1. A method for probing morphology of a tissue using a system including a light source, a polarizer, an analyzer, and a camera with a plurality of picture elements, the method comprising:
   illuminating the tissue with incident light through the polarizer;
   capturing by the camera, through the analyzer, scattered light from the tissue in a time sequence of image frames;
   during said capturing, changing at the same time respective polarization states of said incident light from the light source by varying the polarizer and of said scattered light from the tissue by varying the analyzer;
   during said capturing, detecting for a plurality of picture elements of the camera a time varying intensity signal of the scattered light responsive to the varying polarization state; and
   analyzing the time varying intensity signal for the picture elements throughout the image frames, thereby probing the morphology of the tissue.

2. The method according to claim 1, wherein said illuminating is performed for incident light of different spectral content.

3. The method according to claim 1, wherein said analyzing includes determining light intensity contrast between peaks and troughs of the time varying intensity signal.

4. The method according to claim 1, wherein said analyzing includes determining an intensity differential in time of the time varying intensity signal between image frames.

5. The method according to claim 1, wherein said analyzing includes determining an intensity differential in time of the time varying intensity signal between image frames.

6. The method according to claim 1, wherein said analyzing includes determining a second or higher time derivative of the time varying intensity signal between image frames.

7. The method according to claim 1, wherein said analyzing includes determining a time average of contrasts between frames of the time varying intensity signal.

8. The method according to claim 1, wherein said analyzing includes determining a variance in time of the time varying intensity signal.

9. The method according to claim 1, wherein said analyzing includes performing a transform of the time varying intensity signal to a transformed intensity signal in frequency domain.

10. The method according to claim 1, wherein the time varying intensity signal is an intensity signal periodic in time.

11. A system including a light source, a polarizer, an analyzer, and a camera including an image sensor with a plurality of picture elements, the system configured to:
    illuminate a tissue with incident light through the polarizer;
    capture by the camera through the analyzer, scattered light from the tissue in a time sequence of image frames;
    change at the same time respective polarization states of said incident light from the light source and of said scattered light from the tissue;
    detect for a plurality of picture elements of the camera a time varying intensity signal of the scattered light responsive to the varying polarization state; and
    perform an analysis of the time varying intensity signal for the picture elements throughout the image frames to probe the morphology of the tissue.

12. The system according to claim 11, wherein the analysis of the time varying intensity signal includes a light intensity contrast in time between peaks and troughs of the time varying intensity signal.

13. The system according to claim 11, wherein the analysis of the varying intensity signal includes an intensity differential in time of the time varying signal between image frames.

14. The system according to claim 11, wherein the analysis of the varying intensity signal includes a second or higher derivative in time of the varying intensity signal between the image frames.

15. The system according to claim 11, wherein the analysis of the time varying intensity signal includes a time average of contrasts between frames of the time varying intensity signal.

16. The system according to claim 11, wherein the analysis of the varying intensity signal includes a variance in time of the time varying intensity signal.

17. The system according to claim 11, wherein the analysis of the time varying intensity signal performs a transform of the time varying intensity signal to a transformed intensity signal in frequency domain.

18. The system according to claim 11, further comprising; a mechanism for varying spectral content of the incident light.

19. The system according to claim 11, wherein the time varying intensity signal is an intensity signal periodic in time.

* * * * *